United States Patent [19]

Portoghese

[11] 4,401,672

[45] Aug. 30, 1983

[54] NON-ADDICTIVE NARCOTIC ANTITUSSIVE PREPARATION

[75] Inventor: Philip S. Portoghese, St. Paul, Minn.

[73] Assignee: Regents of the University of Minnesota, Minneapolis, Minn.

[21] Appl. No.: 310,522

[22] Filed: Oct. 13, 1981

[51] Int. Cl.³ .......................................... A61K 31/485
[52] U.S. Cl. .................................................... 424/260
[58] Field of Search ....................................... 424/260

[56] References Cited

U.S. PATENT DOCUMENTS 3,332,950  7/1967  Blumberg et al. ..................... 546/44
4,241,066 12/1980  Kobylecki et al. .................. 424/260
4,241,067 12/1980  Kobylecki et al. .................. 424/260

FOREIGN PATENT DOCUMENTS 2812580 10/1978  Fed. Rep. of Germany .
 751767  7/1956  United Kingdom ................ 424/260

OTHER PUBLICATIONS

Jiang et al., J. Med. Chem., 20(8), pp. 1100–1102 (1977).
Portoghese et al. (I), J. Med. Chem., 21, pp. 598–599 (1978).
Portoghese et al. (II), J. Med. Chem., 22(2), pp. 168–173 (1979).
Portoghese et al. (III), J. Med. Chem., 23(3), pp. 233–234 (3/80).
Caruso et al., Science, 204, pp. 316–318 (4/20/79).

Primary Examiner—Stanley J. Friedman
Attorney, Agent, or Firm—Burd, Bartz & Gutenkauf

[57] ABSTRACT

Non-addictive narcotic antitussive preparations including a normally addictive narcotic analgesic cough suppressive agent and a highly selective long-acting narcotic antagonist in a pharmaceutically acceptable liquid carrier. The narcotic antagonist is an opioid receptor site-directed alkylating agent. Preparations are disclosed having the effectiveness of codeine and other opiates for cough suppression, but devoid of addictive abuse potential.

5 Claims, No Drawings

NON-ADDICTIVE NARCOTIC ANTITUSSIVE PREPARATION

FIELD OF THE INVENTION

1. Background of the Invention

This invention is directed to non-addictive narcotic antitussive preparations and to the method of making and using such preparations. More particularly, the invention is directed to narcotic antitussive preparations containing a highly selective, long-acting narcotic antagonist, such as opioid receptor site-directed alkylating agents, as disclosed in my copending application Ser. No. 245,052, filed Mar. 19, 1981.

2. The Prior Art

Among the drugs employed in the control of cough are those which act by depressing the cough center in the medulla. The most effective and widely used of these antitussives are the narcotic analgesic agents. Codeine, hydrocodone, hydromorphone, and related opiates are most commonly employed for this purpose. One of the side effects of these opiates is their abuse potential. For example, the antitussive preparation, Elixir Terpin Hydrate and codeine, was originally sold throughout the United States over-the-counter as an exempt narcotic, but its abuse led to its being placed on a prescription-only status in many states. Clearly there is a need for a cough preparation having the same effectiveness as codeine or other opiates, but devoid of abuse potential. Although there are some agents such as dextromethorphan, a synthetic antitussive which lacks abuse potential, codeine continues to be the most effective drug prescribed to inhibit the cough reflex.

As described in my aforesaid copending application Ser. No. 245,052, narcotic antagonists have received considerable attention over the past several years, particularly since the discovery of the endorphins. Evidence which supports the concept of multiple opioid receptors and their classification into subtypes, makes it apparent that exogenously administered opioids mediate their manifold effects through several types of receptors. Compounds have been designed that are selective and have prolonged activities due to the attachment of alkylating groups to ligands which are recognized by opioid receptors. The formation of a covalent bond with the receptor enable the drug to remain in the receptor locus and thereby exert its effects for extended periods. The design of such drugs takes into account the location of a nucleophile on the receptor which forms the covalent bond with the reactive group. Compounds produced as the result of such an approach are described, along with the method of making and using them.

SUMMARY OF THE INVENTION

Broadly stated, the present invention comprises a nonaddictive narcotic antitussive preparation including a normally addictive narcotic analgesic agent and a highly selective, long-acting narcotic antagonist in admixture in a suitable liquid carrier. More specifically, the narcotic antagonist is an opioid receptor alkylating agent having the formula:

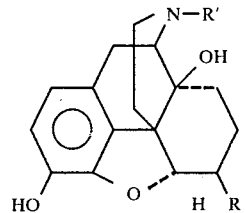

wherein R is a Michael acceptor, a haloacetamide or an isothiocyanate and R' is cyclopropylmethyl, allyl or substituted allyl. The Michael acceptors may be acrylamides or esters of the general formula:

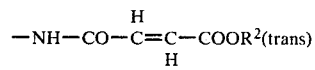

wherein $R^2$ is an alkyl or aralkyl group, and salts thereof. The latter compound is prepared by reaction of $\beta$-naltrexamine with a fumaroyl chloride alkyl or aralkyl ester. The methyl ester has been named funaltrexamine ($\beta$-FNA).

DETAILED DESCRIPTION OF THE PREFERRED EMBODIMENT

In view of the abuse potential of codeine, hydrocodone, hydromorphone, and other opiates as a limitation to their nonprescription use as antitussive agents, the present invention is directed to the addition of a highly selective, long-acting narcotic antagonist to such preparations. Ideally, the narcotic antagonist is highly selective in that the analgesic effects and addiction liability of codeine or other narcotic agents are blocked without destroying their therapeutic effectiveness as antitussive agents. Other narcotic antitussive agents include pholcodeine, ethylmorphine, methadone, dihydrocodeine, and the like, including salts of the narcotic agents.

This is a realistic goal due to the well-known fact that there is a high degree of stereoselectivity in the interaction of opiates with narcotic analgesic receptors. This is in contrast to the antitussive receptors, inasmuch as no stereoselectivity is observed. Thus, the receptors which mediate physical dependence and narcotic analgesia differ considerably from those that mediate inhibition of the cough centers. On this basis, $\beta$-FNA or a similar selective opioid receptor alkylating agent is combined with any of the various narcotic antitussive agents in order to block any abuse potential. Moreover, since $\beta$-FNA and similar alkylating agents appear to act specifically on $\mu$ receptors, which are the sites which mediate the narcotic effects, they are intended to effectively eliminate any abuse potential of a narcotic agent without reducing its antitussive effect. In view of the well documented high specificity of $\beta$-FNA, its combination with a narcotic antitussive affords an effective antitussive with no abuse potential. Pharmacologic studies demonstrate that $\beta$-FNA specifically blocks opiate receptors in vitro and in vivo without affecting other subpopulations ($\kappa,\delta$) of opiate receptors. This blockage is irreversible in vitro and lasts for greater than four days in mice after a single dose. Since it is believed that the addiction liability of opiates is mediated through $\mu$ receptors, it is therefore feasible to block abuse potential without blocking effects mediated through other opiate receptors.

It is well known that there is a high degree of stereoselectivity in the interaction of opiates and other narcotics with opiate receptors which mediate analgesia and addiction liability. Thus, the analgesic activity and addiction liability of narcotic opiates reside principally in one enantiomer. This is in contrast to the comparable antitussive effect exerted by both enantiomers of codeine and synthetic narcotic agents. Moreover, the fact that both enantiomers usually exhibit antitussive activity has permitted the separation of the analgesic activity and abuse potential from the antitussive effect simply by optical resolution.

As disclosed in the aforesaid copending application, $\beta$-FNA can be readily prepared by reaction of $\beta$-naltrexamine with a fumaroyl chloride alkyl or aralkyl ester. The ester moiety may be, for example, methyl, ethyl, propyl, butyl, amyl, etc., or $(CH_2)_n$ Ar wherein $n=1$ to 5 or greater. The Ar substituent may be, for example, phenyl; substituted phenyl wherein the substituent is halogen, hydroxy, nitro, methoxy, methyl, trifluoromethyl, amino, etc.; furane, naphthyl; thiophene and the like. Where R' is allyl or substituted allyl, the starting amine is one containing the allyl or substituted allyl group. In the latter, the substituent may be methyl, ethyl, propyl, halogen, and the like.

Where the Michael acceptor is an acrylamide, the compounds are prepared by reacting $\beta$-naltrexamine with the corresponding acid chloride. R may be, for example, acetylacrylamide, acrylamide, $\alpha$-haloacrylamide in which the halogen is chlorine, iodine or bromine, or the like. Where R is a haloacetamide, $\beta$-naltrexamine is condensed with a haloacetoxysuccinimide in which the halogen is iodine, chlorine or bromine. Where R is isothiocyanate, the compound is prepared by reacting $\beta$-naltrexamine with thiophosgene.

The specificity of $\beta$-FNA for only one type of opiate receptor ($\mu$) makes it ideally suited as an additive to cough preparations which contain codeine, hydrocodone, and other narcotic antitussive agents. In addition, the long duration of action of $\beta$-FNA allows it to be used in relatively small doses, inasmuch as the blockage of $\mu$ opiate receptors by $\beta$-FNA should be a function of the frequency of medication.

Pharmacologic studies indicate dose ratios of antagonist/narcotic should range from 0.01 to 0.5. That is, the alkylating agent narcotic antagonist is present in the cough preparation in amount from 1 percent to 50 percent w/w of the narcotic antitussive agent. The narcotic agent and narcotic antagonist are admixed and presented in a non-toxic pharmaceutically acceptable liquid carrier for oral administration. Typically cough preparations are administered as elixirs in a sweetened aromatic solution of alcohol and water but syrups and other liquid vehicles may be used. Where desirable or necessary, flavoring, preserving, suspending, thickening or emulsifying agents may be included. The solutions may contain antioxidants, buffers, etc.

The antitussive preparations may include other ingredients as commonly found in cough and cold remedies. For example, the preparations may include expectorants such as terpin hydrate, guaifenesin, ammonium chloride, and the like; antihistaminics such as chlorpheniramine maleate, and the like; and anticongestants such as phenylephrine hydrochloride, pseudoephedrine hydrochloride, and the like.

The antagonist/narcotic mixture is present in the vehicle in amount between about 0.03 and 5 percent w/v. The antagonist/narcotic mixture is administered at effective non-toxic cough suppressive dose levels of about 4 to 40 mg/kg/day of body weight given in one dose or several smaller doses throughout the day. The antagonists may be in the form of pharmaceutically acceptable salts, such as salts of organic acids, i.e., lactic, acidic, malic, or p-toluenesulphonic acid, and the like, as well as salts of pharmaceutically acceptable mineral acids, such as hydrochloric or sulphuric acid, and the like.

The invention is further illustrated by the following examples setting forth typical cough suppressive preparations. Although illustrated by use of $\beta$-FNA, other opioid receptor alkylating agents within the scope of the invention may be substituted. The amounts are expressed in mg/5 ml.

EXAMPLE 1

Codeine phosphate 10 mg,
$\beta$-FNA hydrochloride 0.5 mg,
Terpin hydrate 20 mg,
Ethanol 10 percent

EXAMPLE 2

Codeine phosphate 10 mg,
$\beta$-FNA hydrochloride 1 mg,
Guaifenesin 100 mg,
Chlorpheniramine maleate 2 mg,
Ethanol 5 percent

EXAMPLE 3

Codeine phosphate 5 mg,
$\beta$-FNA hydrochloride 0.1 mg,
$NH_4Cl$ 100 mg,
Ethanol 3 percent

EXAMPLE 4

Hydrocodone bitartrate 5 mg,
$\beta$-FNA hydrochloride 1 mg,
Guaifenesin 50 mg,
Phenylephrine hydrochloride 5 mg,
Ethanol 10 percent

EXAMPLE 5

Hydromorphone hydrochloride 1 mg,
$\beta$-FNA hydrochloride 0.5 mg,
Pseudoephedrine hydrochloride 30 mg,
Chlorpheniramine maleate 2 mg,
Guaifenesin 100 mg,
Ethanol 3 percent It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A non-addictive narcotic antitussive preparation comprising:
   (A) a normally addictive narcotic analgesic cough suppressive agent selected from the group consisting of codeine, hydrocodone, hydromorphone, pholcodeine, ethylmorphine, methadone and dihydrocodiene;
   (B) a highly selective long-acting opioid receptor site-directed narcotic antagonist alkylating agent having the formula:

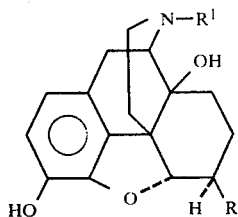

Wherein R is acetylacrylamide, acrylamide, or α-haloacrylamide wherein the halogen is chlorine, iodine or bromine, a haloacetamide: NHCO—CH₂X wherein X is iodine, chlorine or bromine, isothiocyanate and esters, said esters having the general formula:

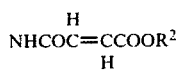

wherein $R^2$ is $(CH_2)_nH$ or $(CH_2)_nAr$, wherein Ar is phenyl, furane, naphthyl, thiophene or substituted phenyl wherein the substituent is halogen, hydroxy, nitro, methoxy, methyl, trifluoromethyl or amino, and n is 1 to 5; and R' is cyclo-propylmethyl, allyl and substituted allyl, the substituent of which is methyl, ethyl, propyl or halogen; and pharmaceutically acceptable salts thereof; and (C) a pharmaceutically acceptable liquid carrier, the antagonist alkylating agent being present in amount from about 1 to 50% w/w of the narcotic cough suppressive agent, and the antagonist/narcotic mixture being present in the carrier in amount between about 0.03 to 5% w/v.

2. An antitussive preparation according to claim 1 wherein R' is cyclopropylmethyl and $R^2$ is methyl.

3. An antitussive preparation according to claim 1 wherein R is isothiocyanate.

4. An antitussive preparation according to claim 1 wherein R' is cyclopropylmethyl.

5. An antitussive preparation according to claim 1 wherein R' is allyl or substituted allyl.

* * * * *